United States Patent [19]

Yoshimura et al.

[11] 4,417,079

[45] * Nov. 22, 1983

[54] PROCESS FOR PRODUCING NORMAL-OCTANOL

[75] Inventors: Noriaki Yoshimura; Masuhiko Tamura, both of Okayama, Japan

[73] Assignee: Kuraray Company, Limited, Kurashiki, Japan

[*] Notice: The portion of the term of this patent subsequent to Oct. 26, 1999 has been disclaimed.

[21] Appl. No.: 347,558

[22] Filed: Feb. 10, 1982

[30] Foreign Application Priority Data

Feb. 16, 1981 [JP] Japan .................................. 56-21695

[51] Int. Cl.$^3$ ..................... C07C 31/125; C07C 29/17
[52] U.S. Cl. ...................................... 568/903; 568/840
[58] Field of Search ................................ 568/840, 903

[56] References Cited

U.S. PATENT DOCUMENTS

| | | | |
|---|---|---|---|
| 3,407,224 | 10/1968 | Smutny | 568/840 |
| 3,670,032 | 6/1972 | Romanelli | 568/840 |
| 3,887,627 | 6/1975 | Romanelli | 568/840 |
| 3,992,456 | 11/1976 | Atkins et al. | 568/903 |
| 4,142,060 | 2/1979 | Kuntz | 568/840 |

*Primary Examiner*—J. E. Evans

*Attorney, Agent, or Firm*—Oblon, Fisher, Spivak, McClelland & Maier

[57] ABSTRACT n-Octanol is obtained by (i) reacting butadiene with water in a solution containing water, a carbonate and/or bicarbonate salt of a monodentate tertiary amine, and sulpholane in the presence of a palladium compound and a hydrophilic monodentate phosphine, to form 2,7-octadien-1-ol; (ii) extracting 2,7-octadien-1-ol from at least part of the reaction mixture obtained in step (i) with a saturated aliphatic hydrocarbon, a monoolefinic hydrocarbon or an alicyclic hydrocarbon, and recycling the extraction residue to the 2,7-octadien-1-ol synthesis step (i); (iii) subjecting the extract layer containing 2,7-octadien-1-ol as obtained in step (ii) to distillation to distill off a large proportion of the extracting solvent therefrom, followed by distillation in the presence of water, whereby the extracting solvent remaining is distilled off in the form of an azeotropic mixture with water, to obtain a distillation residue; (iv) recovering 2,7-octadien-1-ol from the distillation residue obtained in step (iii) by distillation; (v) hydrogenating the 2,7-octadien-1-ol obtained in step (iv) in the presence of a hydrogenation catalyst to obtain n-octanol; and (iv) recovering n-octanol from the hydrogenation reaction mixture by distillation.

15 Claims, No Drawings

PROCESS FOR PRODUCING NORMAL-OCTANOL

BACKGROUND OF THE INVENTION

1. Field of the Invention

This invention relates to a process for producing n-octanol by reacting butadiene and water followed by hydrogenation of the resulting 2,7-octadien-1-ol. These reactions are illustrated by the following equations:

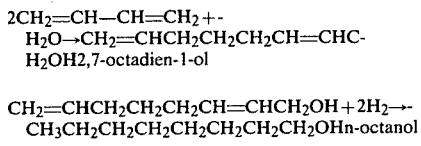

$2CH_2=CH-CH=CH_2 + H_2O \rightarrow CH_2=CHCH_2CH_2CH_2CH=CHCH_2OH$
2,7-octadien-1-ol $CH_2=CHCH_2CH_2CH_2CH=CHCH_2OH + 2H_2 \rightarrow CH_3CH_2CH_2CH_2CH_2CH_2CH_2CH_2OH$
n-octanol Normal-octanol is very useful as a starting material for the production of various industrial products. However, the quantity of n-octanol currently consumed is not large since there is no established commercial process capable of producing n-octanol at a low cost. At present, n-octanol is produced only on a relatively small scale by hydrolyzing natural glycerides followed by esterification and hydrogenation.

2. Description of the Prior Art

It has been proposed to prepare n-octanol by reacting butadiene with water in the presence of a palladium catalyst to synthesize 2,7-octadien-1-ol followed by hydrogenation of 2,7-octadien-1-ol (U.S. Pat. No. 3,670,032). Since, as is well known, the palladium catalyst to be used in the synthesis of 2,7-octadien-1-ol is very expensive, solution of the following technological problems (1)–(5) is essential to produce n-octanol production on a commercial scale in accordance with the above-mentioned proposal:

(1) Achieving a high reaction rate at a palladium catalyst concentration within the range acceptable from the industrial viewpoint.

(2) Obtaining a sufficiently high selectivity toward 2,7-octadien-1-ol.

(3) Maintaining the palladium catalyst activity without deterioration for a prolonged period.

(4) Separating 2,7-octadien-1-ol from the reaction mixture efficiently without causing a substantial decrease in activity of the palladium catalyst. According to the proposal so far made, 2,7-octadiene-1-ol is recovered by direct distillation of the reaction mixture which contains the palladium catalyst, but an intensive study by the present inventors has revealed that when the distillation temperature exceeds about 120° C., the palladium catalyst becomes deactivated because of reduction to the metallic state.

(5) Retaining the catalytic activity of the palladium catalyst even after the step of separating 2,7-octadien-1-ol from the reaction mixture.

However, the prior art methods have failed to solve these technological problems. Accordingly, a need continues to exist for a commercial process for producing n-octanol from butadiene.

SUMMARY OF THE INVENTION

Accordingly, it is in object of this invention to provide a process for preparing n-octanol from butadiene at commercially acceptable palladium catalyst concentrations in the reaction medium.

It is another object of the present invention to achieve a process having a high selectivity for 2,7-octadien-1-ol when reacting butadiene with water.

A further object of this invention is to provide a process wherein the palladium catalyst remains active for long periods.

Still another object of this invention is to provide a method of recovering 2,7-octadien-1-ol from the reaction mixture of water, butadiene and palladium catalyst wherein the deactivation of the catalyst is avoided and the catalyst activity is maintained at a high level.

These and other objects of the present invention which will be apparent from the following disclosure have been achieved by a process comprising:

(i) reacting butadiene with water in a solution containing water, a carbonate and/or bicarbonate salt of a mondentate tertiary amine having a basicity constant (pKa) of not less than 7, and sulfolane in the proportions of 25–55 percent, 5–30 percent and 30–65 percent by weight based on the reaction mixture, respectively, in the presence of a palladium compound and a hydrophilic monodentate phosphine in an amount of at least 6 moles per gram atom of palladium, to form 2,7-octadien-1-ol;

(ii) extracting 2,7-octadien-1-ol from at least part of the reaction mixture obtained in step (i) with a saturated aliphatic hydrocarbon, a monoolefinic hydrocarbon or an alicyclic hydrocarbon, and recycling the extraction residue to the 2,7-octadien-1-ol synthesis step (i);

(iii) subjecting the extract layer containing 2,7-octadien-1-ol as obtained in step (ii) to distillation at a liquid phase temperature of not higher than about 100° C. to distill off a large proportion of the extracting solvent therefrom, followed by distillation in the presence of water, whereby the extracting solvent remaining is distilled off in the form of an azeotropic mixture with water, to obtain a distillation residue;

(iv) recovering 2,7-octadien-1-ol from the distillation residues obtained in step (iii) by distillation;

(v) hydrogenating the 2,7-octadien-1-ol obtained in step (iv) in the presence of a hydrogenation catalyst to obtain n-octanol; and (vi) recovering n-octanol from the hydrogenation reaction mixture by distillation.

The process of the invention not only produces 2,7-octadien-1-ol at a high rate of reaction and a high selectivity but also makes it possible to separate 2,7-octadien-1-ol from the reaction mixture without causing decrease in activity of the palladium catalyst whereby the palladium catalyst may be recycled for a repeated use. The process of the invention also can give highly pure n-octanol in a very high yield. Consequently, the process of the invention can produce n-octanol using butadiene, water and hydrogen as the raw materials in an industrially advantageous manner.

DETAILED DESCRIPTION OF THE INVENTION

The palladium compound to be used in the process of the invention for producing 2,7-octadien-1-ol may be any of the palladium compounds known or proposed to be suitable for synthesizing 2,7-octadien-1-ol. Examples of the usable palladium compound are palladium acetylacetonate, II-allylpalladium acetate, II-allylpalladium chloride, palladium acetate, palladium carbonate, palladium nitrate, palladium chloride, sodium chloropalladate, bis(benzonitrile)palladium chloride, bis(triphenylphosphine)palladium chloride, bis(triphenylphosphine)- palladium acetate, bis(1,5-cyclooctadiene)palladium and bis(II-allyl)palladium. Since the actual catalytically active species in the 2,7-octadien-1-ol synthesis reaction are complexes of lower-valence palladium, a compound of divalent palladium, when used as the catalyst, may be reduced by the phosphine or butadiene present in the reaction system, so that an active complex may be formed. The active catalyst species may also be formed beforehand by reacting said divalent palladium compound with a reducing agent in the reaction system for octadienol synthesis or in a separate reaction vessel. The reducing agent usable for such purpose includes among others alkali metal hydroxides, alkali metal carboxylates, sodium borohydride, zinc powder, magnesium, and hydrazine. Although the amount of the palladium compound is not critical, and any catalytically effective amount may be used, it is preferable to employ a palladium concentration of from 0.1–50, more preferably 0.5–20, milligram atoms per liter of the reaction mixture.

The hydrophilic monodentate phosphine as described herein includes those phosphine compounds which are capable of being dissolved in water under the reaction conditions and are represented by the general formula

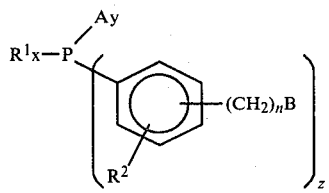

wherein $R^1$ is an aliphatic, alicyclic, or substituted or nonsubstituted aromatic hydrocarbon group containing up to 8 carbon atoms; $R^2$ is a hydrogen atom, a methyl, nitro, cyano or methoxy group or a halogen atom; n is an integer of 0 or 1, x is an integer of 0, 1 or 2, y and z are each an integer of 0, 1, 2, or 3 with the proviso that y and z are not concurrently equal to 0 and that $x+y+z=3$; A is —CH$_2$CH(CH$_3$)COOM, —C(CH$_3$)$_2$COOM, —CH$_2$CH(CH$_3$)N(R$^3$)(R$^4$), —C(CH$_3$)$_2$N(R$^3$)(R$^4$), a carbonate or bicarbonate or —CH$_2$CH(CH$_3$)N(R$^3$)(R$^4$) or a carbonate or bicarbonate of —C(CH$_3$)$_2$N(R$^3$)(R$^4$); B is —SO$_3$M, —COOM, —N(R$^3$)(R$^4$) or a carbonate or bicarbonate of —N(R$^3$)(R$^4$); R$^3$ and R$^4$ each being methyl, ethyl or n-propyl and M being an alkali metal.

In general formula (I), $R^1$ is a hydrocarbon group containing 1–8 carbon atoms, more specifically, such an aliphatic hydrocarbon group as methyl, ethyl, n-propyl, isopropyl, n-butyl, tert-butyl or n-octyl, such an alicyclic hydrocarbon group as cyclohexyl or methylcyclohexyl, or such an aromatic hydrocarbon group as phenyl, benzyl or tolyl. The aromatic hydrcarbon group may have one or more substituents each selected from the group consisting of methoxy, chlorine atom, cyano and nitro.

Referring to B in general formula (I), when B is —SO$_3$M or —COOM, M is an alkali metal, preferably sodium, potassium or lithium. When B is general formula (I) is —SO$_3$M or —COOM, the phosphine takes the form of an alkali metal salt and generally is used as such. Alternatively, such alkali metal salt may be prepared by reacting the phosphine in the form of a carboxylic or sulfonic acid or an ester thereof with an alkali metal hydroxide or an alkali metal salt (e.g., bicarbonate or carbonate) in the reaction system or a separate reaction vessel.

Among the monodentate phosphines of general formula (I), preferred are those diaryl- and triarylphosphines in which $R^1$ is an aromatic hydrocarbon group; n is an integer of 0 or 1, x is an integer of 0, 1 or 2, y is an integer of 0 or 1 and z is an integer of 0, 1, 2, or 3, with the proviso that y and z are not concurrently equal to 0 and that $x+y+z=3$; A is —CH$_2$CH(CH$_3$)COOM; B is —SO$_3$M, —COOM, —N(R$^3$)(R$^4$) or a carbonate or bicarbonate or —N(R$^3$)(R$^4$). Specific examples are as follows:

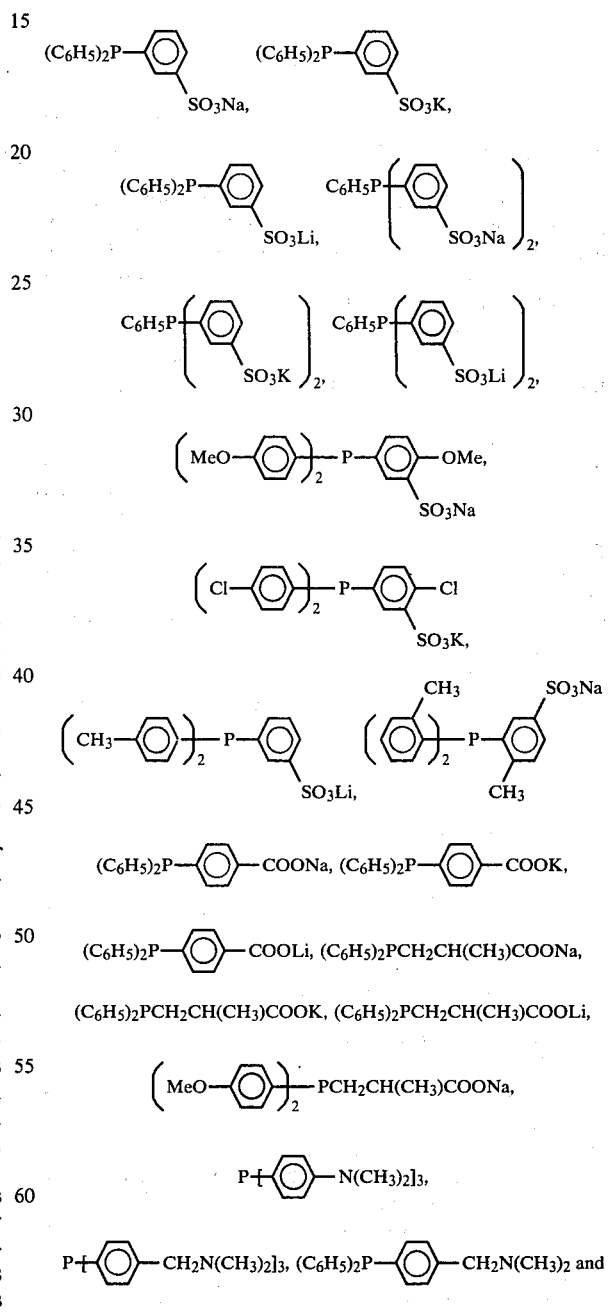

Among these, the following are especially preferred hydrophilic monodentate phosphines:

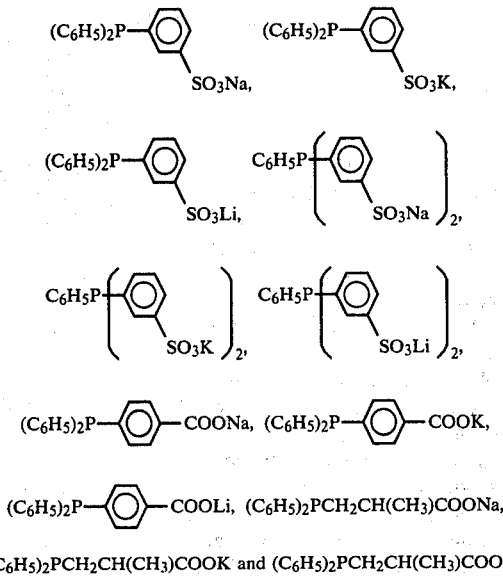

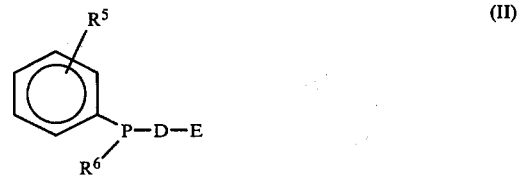

Of the hydrophilic monodentate phosphines of general formula (I), those which contain an amino group (strictly a substituted amino) are added to the reaction system generally as they are. However, in the reaction system, they take the form of carbonates or bicarbonates, and therefore carbonates or bicarbonates of amino-containing phosphines may be prepared separately for addition to the reaction system. The phosphines may be used either alone or in combination of any two or more of them. From the viewpoints of rate of reaction, selectivity toward 2,7-octadien-1-ol, life of palladium catalyst, and elution of palladium into the extractant layer in step (ii), the hydrophilic monodentate phosphine should be used in an amount of at least 6 moles, preferably 10 moles or more, per gram atom of palladium. Whereas there is no strict upper limit to the phosphine amount, generally it is preferably to use the phosphine in an amount of not more than 150 moles, more preferably 10-100 moles, per gram atom of palladium. In the prior art, it has been believed that when the amount of a phosphine used as a ligand for the purpose of retaining the life of a palladium catalyst exceeds 5 moles per gram atom of palladium, the rate of reaction decreases markedly and at the same time the selectivity toward 2,7-octadien-1-ol decreases [Chem. Commun., 330 (1971)]. Surprisingly, it has now been found that, by combined use of a hydrophilic monodentate phosphine and sulfolane in accordance with the present invention, the reaction rate and selectivity can be retained at high levels even when the phosphine is used in large excess as compared with palladium. Since the phosphine can be used in large excess, the activity of the palladium catalyst can remain constant for a prolonged period of time and in addition the elution of palladium into the extractant layer in the subsequent step (ii) can be reduced to a minimum.

According to the findings by the present inventors, hydrophilic monodentate phosphines tend to be oxidized to the corresponding phosphine oxides by a trace amount of oxygen present in the reaction system, resulting in failure in function thereof. The present inventors have now found that such oxidation of hydrophilic monodentate phosphines can be suppressed by adding, in combination with such a phosphine, a hydrophilic bidentate phosphine in an amount of 0.3-3 moles per gram atom of palladium. Moreover, the use of such hydrophilic bidentate phosphine brings about an increase in thermal stability of the palladium catalyst, hence stabilization of the catalytic activity over a prolonged period. When the amount of the bidentate phosphine is less than 0.3 mole per gram atom of palladium, substantial effects of the addition thereof are no more produced, whereas, in an amount exceeding 3 moles, the bidentate phosphine causes a marked decrease in rate of reaction. The hydrophilic bidentate phosphine includes, among others, those represented by the general formula (II) shown below and capable of being dissolved in water under the reaction conditions:

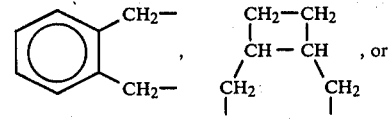

wherein $R^5$ is a hydrogen or halogen atom, a methyl, cyano, methoxy or nitro group, $-SO_3M$, $-COOM$, $-N(R^7)(R^8)$, $-CH_2N(R^7)(R^8)$, a carbonate or bicarbonate of $-N(R^7)(R^8)$ or a carbonate or bicarbonate or $-CH_2N(R^7)(R^8)$; $R^7$ and $R^8$ each being methyl, ethyl or n-propyl and M being an alkali metal, $R^6$ is a hydrocarbon group containing up to 8 carbonatoms, D is $-(CH_2)_n-$, n being an integer of 1 through 4,

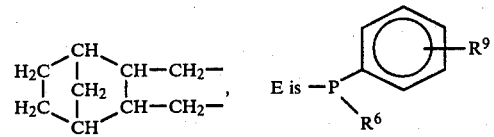

$R^9$ being $-SO_3M$, $-COOM$, $-N(R^7)(R^8)$, $-CH_2N(R^7)(R^8)$, a carbonate or bicarbonate of $-N(R^7)(R^8)$ or a carbonate or bicarbonate of $-CH_2N(R^7)(R^8)$; $-N(R^7)(R^8)$, a carbonate or bicarbonate or $-N(R^7)(R^8)$, or $-COOM$. In general formula (II), M in $-SO_3M$ and $-COOM$ represented by $R^5$, E or $R^9$ is an alkali metal, preferably sodium, potassium or lithium. The $C_{1-8}$ hydrocarbon group represented by $R^6$ includes such aliphatic hydrocarbon groups as methyl, ethyl, propyl, isopropyl, butyl, tertbutyl and octyl, such alicyclic hydrocarbon groups as cyclohexyl, and such aromatic hydrocarbon groups as phenyl, benzyl and tolyl. Among these, phenyl is especially preferred. The following are examples of the bidentate phosphine:

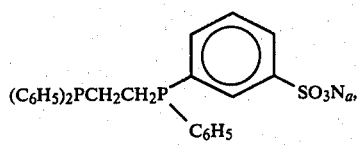

-continued

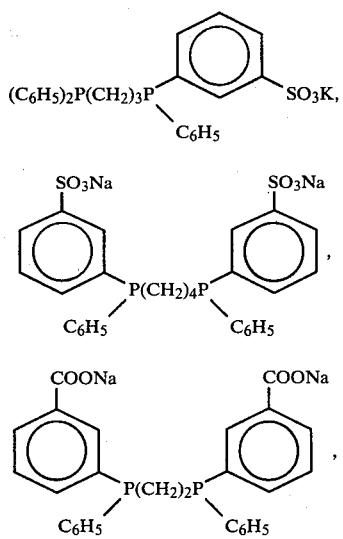

(C₆H₅)₂PCH₂N(CH₃)₂, (C₆H₅)₂P(CH₂)₂N(C₂H₅)₂ and
(C₆H₅)₂PCH₂CH₂COOK.

The bidendate phosphines may be used either alone or in combination of any two or more of them.

The use of the monodentate tertiary amine carbonate and/or bicarbonate in step (i) of the process in accordance with the invention causes a marked increase in rate of reaction while holding the selectivity toward 2,7-octadien-1-ol at a high level, achieves stabilization of the catalytic activity of the palladium catalyst, and improves the extractability of 2,7-octadien-1-ol in the subsequent step (ii). The monodentate tertiary amine must have a basicity constant (pKa) of not less than 7, and specifically includes, among others, trimethylamine, triethylamine, tri-n-butylamine, 1-N,N-dimethylamino-2-propanol, N,N-dimethyl-2-methoxyethylamine, N-methylmorpholine and N,N,N',N'-tetramethylhexamethylenediamine. Among these, triethylamine is especially preferred from the viewpoints of results of reaction, boiling point, solubility, price and so on. The above-mentioned effects producible by the addition of the specific tertiary amine carbonate and/or bicarbonate cannot be obtained with carbonates and/or bicarbonates of monodentate or bidentate tertiary amines having a pKa value of less than 7, such as pyridine and dipyridyl, or with carbonates and/or bicarbonates of those tertiary amines which have a pKa value of 7 or higher but are highly capable of serving as bidentate ligands, such as N,N,N',N'-tetramethyldiaminoethane and N,N-dimethyl-2-aminopropionitrile.

In the reaction system, the tertiary amine carbonate and/or bicarbonate takes the form of an equilibrium mixture of the amine carbonate and/or bicarbonate itself, the carbonate and/or bicarbonate ion and the tertiary amine (cf. the equilibrium equation given below), and the proportion of the tertiary amine carbonate and/or bicarbonate present under the reaction conditions depends upon the temperature and the absolute partial pressure of carbon dioxide.

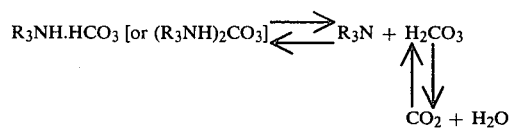

Therefore, generally, the reaction is carried out under pressure so as to maintain the absolute partial pressure of carbon dioxide at about 1–10 kg/cm². Considering reaction results, extraction efficiency, migration of the tertiary amine into the extractant layer and so on, the tertiary amine carbonate and/or bicarbonate should be used in an amount of 5–30 percent by weight based on the reaction mixture.

Any commercially available butadiene may be used, for example polymerization grade butadiene, chemical reaction grade butadiene, or a butadiene-containing hydrocarbon mixture (the so-called C₄ fraction). From the viewpoints of reaction rate and easy recovery of unreacted butadiene, polymerization grade one and chemical reaction grade one are preferred. The amount of butadiene is not critical. However, there is a limit in solubility of butadiene in aqueous sulfolane, so that excess butadiene would form a separate layer within the reaction system. Therefore, the reaction is generally carried out by introducing butadiene continuously or intermittently into the reaction system so as to maintain the proportion of butadiene of 0.1–10 percent, preferably 1–5 percent, by weight based on the reaction mixture.

In the practice of the process of the present invention, the concentration of 2,7-octadien-1-ol in the reaction mixture has a great influence upon rate of extraction of 2,7-octadiene-1-ol in step (ii), yield of byproducts, and elution of sulfolane and catalyst components into the extractant layer, for instance, and it is therefore desirable that the 2,7-octadiene-1-ol concentration in the reaction mixture to be fed to step (ii) should be maintained within the range of 0.3–2 moles per liter of the reaction mixture. The amount of water, which is contained in the aqueous sulfolane solution in the reaction system, should preferably be in the range of 25–55 percent by weight based on the reaction mixture from the viewpoints of solubility of butadiene in the aqueous sulfolane solution and efficient extraction of 2,7-octadien-1-ol. When the amount of water exceeds 55 percent by weight, the reaction of butadiene with water becomes markedly slow. On the other hand, when the amount of water is less than 25 percent by weight, the extractability of 2,7-octadien-1-ol in step (ii) falls and the elution of sulfolane and catalyst components into the extractant layer increases. Generally, the reaction in step (i) is carried out at a temperature of 50°–110° C. The reactor may be any of known gas-liquid contact reactors, for example a stirred tank reactor or a bubble cap tower reactor.

In the process of the invention, the reaction mixture obtained in step (i) and containing 2,7-octadien-1-ol is subjected to extraction in the next step (ii). As the extraction apparatus, there may be used such one for general industrial purposes as a stirred tower type extractor, an RDC tower extractor or a perforated plate tower. Generally, the extraction is carried out at a temperature of 60° C. or below in an atmosphere of carbon dioxide and/or such an inert gas as nitrogen, helium or argon. In particular, when the extraction is conducted under carbon dioxide atmosphere, migration or dissolution of the catalyst components and tertiary amine into the extractant layer can be efficiently suppressed.

The extractant to be used includes saturated aliphatic hydrocarbons, monoolefinic hydrocarbons and alicyclic hydrocarbons, each having a lower boiling point than that of 2,7-octadien-1-ol. Examples are n-butane, isobutane, butene, isobutene, n-pentane, n-hexane, cyclohexane, cyclohexene, n-heptane, methylcyclohexane, n-octane, isooctane and a mixture of butane, butene isobutene and others which are contained in the $C_4$ fraction used as the butadiene source. Among these, n-pentane, n-hexane, cyclohexane and methylcyclohexane are particularly preferred. For achieving effective extraction of 2,7-octadien-1-ol and minimizing dissolution or migration of the catalyst components and sulfolane into the extractant layer, the extractant is used in an amount of 0.3-3 parts by volume per part by volume of the reaction mixture from the 2,7-octadien-1-ol synthesis step. The extraction residue obtained in step (ii), which contains the catalyst components, is recycled to the 2,7-octadien-1-ol synthesis step (i.e., step (i)) for reuse. If desired, part of the extraction residue may be separated, treated for catalyst regeneration, and then recycled to step (i). In step (ii), the products, namely 2,7-octadien-1-ol, 1,7-octadien-3-ol, dioctadienyl ether, 1,3,7-octatriene, high-boiling byproducts and others, primarily migrate into the extractant layer. The extract layer also contains unreacted butadiene, and small amounts of sulfolane, the tertiary amine carbonate and/or bicarbonate, the palladium catalyst, the phosphine, water, and so on. The extracting solvent is removed from the extract layer containing 2,7-octadien-1-ol as obtained in step (ii) by subjecting said extract layer to distillation at a liquid phase temperature of not higher than about 100° C. to distill off a large proportion (generally more than 75 percent) of the extracting solvent therefrom, followed by azeotropic distillation in the presence of water, whereby the extracting solvent remaining is distilled off in the form of an azeotropic mixture with water (step (iii)). It is also possible to remove part of the sulfolane, tertiary amine carbonate and/or bicarbonate and catalyst components contained in the extract layer obtained in step (ii) by washing said layer with a small amount of water prior to the treatment in step (iii) and feed the washed extract layer to step (iii) while recycling the aqueous layer to step (i). In step (iii), if the extract layer contains a relatively low-boiling extracting solvent, most of the extracting solvent may be distilled off by distillation at a liquid phase temperature not exceeding 100° C. without addition of water. The amount of water should be such that the liquid phase temperature is always maintained at about 100° C. or below. The method of removing the extracting solvent by distillation in the presence of water has, among others, the following advantages: (1) thermal degradation of the trace amounts of the palladium catalyst contained in the extract layer can suppressed since the liquid phase temperature can be maintained at about 100° C. or below; (2) stabilized continuous operation of an industrial plant can easily be achieved. It is not impossible to recover the extracting solvent, 2,7-octadien-1-ol, sulfolane and so on from the extract layer obtained in step (ii) by usual distillation, but the usual distillation method is inherently disadvantageous in: (1) requiring a high liquid phase temperature which causes thermal degradation of the palladium catalyst; (2) distillation under reduced pressure is eventually needed; (3) stability of operation is poor. When compared with this method, superiority of the previously mentioned method of removing the extracting solvent by distillation in the presence of water will become evident. In case the distillation residue obtained in step (iii) contains water in an amount exceeding the limit of solubility, allowing the distillation residue stand results in separation thereof into an organic layer predominantly composed of 2,7-octadien-1-ol and an aqueous layer containing the sulfolane and catalyst components. In this case, the aqueous layer, which contains sulfolane and catalyst components, can be returned to step (i) for reuse thereof, if desired following treatment of part thereof for catalyst regeneration. Recovery of 2,7-octadien-1-ol from the distillation residue obtained in step (iii) is carried out by distillation (step (iv)). The distillation in step (iv) is conducted generally at a liquid phase temperature of 100° C. to about 200° C. In this distillation, 1,7-octadien-3-ol is distilled off along with 2,7-octadien-1-ol. However, separation of them from each other by fractional distillation is not always necessary; they may be recovered in the form of a mixture and then hydrogenated as such in the next step (v). The distillation residue obtained in step (iv) is substantially composed of sulfolane, dioctadienyl ether, high-boiling byproducts and trace amounts of catalyst components, and if desired, it is treated for recovery of valuable components. Individual recovery of sulfolane and dioctadienyl ether from the distillation residue by distillation is possible but not easy because they have close boiling points. Therefore, it is advisable to add to the distillation residue a practically equal amount of water or a mixture of water and the extractant to be used in step (ii) and, after intimate contact, allowing the mixture to stand so as to cause separation into an aqueous layer containing the catalyst components and sulfolane and an organic layer containing dioctadienyl ether, high boiling byproducts and, in some instances, the extractant. The aqueous layer obtained is subjected to treatment with activated carbon, for instance, so as to remove the catalyst components, and then returned to step (i) or step (iii) for reuse. It is also possible to recover sulfolane (and a small amount of dioctadienyl ether) from the aqueous layer by distillation. From the organic layer, there can be recovered highly pure dioctadienyl ether, 2,7-octadien-1-ol and, in some cases, the extractant.

In the process of the invention, it is preferable that the sum of the amount of water consumed in step (i) and the amounts of water respectively consumed in the subsequent steps should be proportionate to the amount of water added to the process in step (iii), for instance. The 2,7-octadien-1-ol or mixture of 2,7-octadien-1-ol and 1,7-octadien-3-ol as obtained in step (iv) is subjected in step (v) to conventional hydrogenation in the presence of a hydrogenation catalyst. Generally, the hydrogenation is carried out at a temperature from room temperature to about 200° C. at a hydrogen pressure of 1–100 atmospheres. As the hydrogenation catalyst, there may be used any of known ones including palladium-on-carrier, Raney nickel, modified Raney nickel, nickel-on-carrier and ruthenium. When palladium-on-carrier, Raney nickel or modified Raney nickel is used, the reaction is preferably carried out at a temperature within the range of room temperature to 130° C. since, at such temperature, side reactions can be minimized and the catalytic activity can be retained for a prolonged period of time. When a nickel-on-carrier catalyst is used, the reaction is conducted generally at a hydrogen pressure of 1–100 atmospheres and a reaction temperature of about 100°–200° C. In this case, the heat of reaction can advantageously be recovered as steam. The palladium-on-carrier catalyst includes known general-purpose ones in which palladium is supported on a carrier such as activated carbon, barium sulfate, silica, or alumina. The modified Raney nickel catalyst includes among others those Raney nickel catalysts modified with metals such as chromium, tungsten, molybdenum, rhenium, zirconium, manganese, cobalt, titanium and/or iron. The nickel-on-carrier catalyst includes one in which nickel is supported on a carrier such as diatomaceous earth, alumina or silica. The nickel-on-carrier catalyst may be modified with another metal such as cobalt, manganese, chromium, copper and/or zirconium.

The hydrogenation can advantageously be carried out with the raw material diluted with the hydrogenation product. Alternatively, the raw material may be diluted with an organic solvent. The organic solvent usable for said purpose includes among others n-pentane, n-hexane, n-octane, cyclohexane, diethyl ether, tetrahydrofuran, methanol, ethanol, n-butanol and n-hexanol. The hydrogenation may be conducted either batchwise or continuously. For commercial production, continuous hydrogenation is preferred. When the hydrogenation is performed continuously, it is preferable, to obtain highly pure n-octanol, to employ the reaction scheme comprising two steps, first a preliminary hydrogenation step and a finishing hydrogenation step. In such continuous hydrogenation, preliminary hydrogenation is carried out in the liquid phase in a stirred tank reactor or a bubble tower reactor in the presence of a palladium-on-carrier, Raney nickel, modified Raney nickel or nickel-on-carrier catalyst, for instance, or in the gaseous or liquid phase in a tower reactor packed with a palladium-on-carrier or nickel-on-carrier catalyst. When the hydrogenation is carried out in a stirred tank reactor or a bubble tower reactor, the catalyst is used in an amount, calculated as the metal, of 0.01–10 percent by weight of the liquid reaction mixture. In the preliminary hydrogenation step, the raw material is hydrogenated to a conversion rate of at least 90 percent, preferably at least 95 percent, without regard to the type of reactor and the kind of catalyst. The reaction mixture from the preliminary hydrogenation step is, if necessary after removal of the catalyst, subjected to finishing hydrogenation. Since the reaction mixture from the preliminary hydrogenation reactor generally contains a small amount of octenols and a trace amount of carbonyl compounds, the finishing hydrogenation is preferably carried out in the presence of a nickel catalyst or a ruthenium-on-carrier catalyst. Especially when carried out in the gaseous or liquid phase in a tower reactor packed with a nickel-on-carrier or ruthenium-on-carrier catalyst, the hydrogenation reaction can proceed to substantial completion. The finishing hydrogenation can optimally be conducted at a temperature of about 100° to about 200° C. and a hydrogen pressure of about 1–50 atmospheres. n-Octanol is recovered from the reaction mixture from the finishing hydrogenation step by distillation (step (vi)). The hydrogenation catalyst may be removed from said reaction mixture prior to distillation. When a mixture of 2,7-octadien-1-ol and 1,7-octadien-3-ol is hydrogenated in step (v), 3-octanol and n-octanol are obtained in step (vi). The distillation in step (vi) is generally performed at a temperature of 120°–200° C.

The 2,7-octadien-1-ol synthesized in step (i) of the process of the invention may also be converted to n-octanal and n-octanol by hydrogenation and isomerization in the liquid phase in the presence of a palladium catalyst. n-Octanal is useful as a perfumery or flavor chemical and as the intermediate for producing caprylic acid, n-octylamine, di-n-octylamine, tri-n-octylamine, 2-hexyl-1-decanol, 2-hexyldecanoic acid, etc. (cf. Japanese Patent Application No. 188,777/80).

Having generally described this invention, a further understanding can be obtained by reference to certain specific examples which are provided herein for purposes of illustration only and are not intended to be limiting unless otherwise specified.

EXAMPLE 1

(1) Synthesis of 2,7-octadien-1-ol and separation thereof from the reaction mixture Using the apparatus mentioned below, the 2,7-octadien-1-ol synthesis reaction followed by extraction with n-hexane was repeatedly carried out. The whole procedure was continuously performed to avoid entering of air into the system. The atmosphere in sulfolane, water and n-hexane were replaced with nitrogen gas.

Reactor:
A one-liter stainless steel autoclave equipped with thermometer, magnetic stirrer, butadiene metering and feeding pump, gas inlet/outlet and liquid inlet/outlet.

Extractor:
A 2-liter pressure glass autoclave equipped with thermometer, magnetic stirrer, gas inlet/outlet and liquid inlet/outlet. The extractor was connected directly to the liquid outlet of the above-mentioned reactor with a pipe.

Means for washing with water:
A three-necked flask equipped with stirrer, gas inlet/outlet and liquid inlet/outlet. The washing device was connected directly to the above reactor and extractor respectively by piping.

The above reactor was charged with 310 g of sulfolane, 240 g of distilled water, 44 g of triethylamine (corresponding to 71 g of triethylamine bicarbonate), 466 mg (3.8 millimoles/liter of the whole liquid charge) of palladium acetate, and 18.5 g (85 millimoles/liter of the whole liquid charge) of sodium m-(diphenylphosphino)-benzenesulfonate dihydrate (for formula, see below). The system was sufficiently

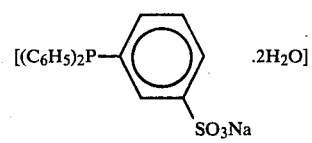

purged with carbon dioxide and then carbon dioxide was introduced with stirring so as to convert triethylamine into triethylamine bicarbonate. The system was then pressurized to 8 kg/cm² (gauge) with carbon dioxide. The system was heated with stirring at the rate of 600 rpm (revolutions per minute), and, after the system reached the temperature of 80° C., the reaction was conducted by introducing liquified butadiene continuously at the rate of 70 grams per hour at 80° C. for an hour. Then, the butadiene feeding and stirring were stopped, and, while cooling, the whole reaction mixture was fed to the extractor by utilizing of the carbon dioxide pressure. After addition of 250 ml of n-hexane to the mixture, the system was pressurized to 3 kg/cm² (gauge) with carbon dioxide. Extraction was effected by stirring the contents at the rate of 600 rpm at 40° C. for 15 minutes. After stopping the stirring, the contents were allowed to stand for 10 minutes. The resulting upper n-hexane layer was fed to the washing device by taking advantage of the carbon dioxide pressure. The lower layer (extraction residue) was again subjected to the same extraction procedure with 250 ml of n-hexane, and the n-hexane layer was fed under pressure to the washing device. The extraction residue containing the catalyst components was fed to the 2,7-octadien-1-ol synthesis reactor by taking advantage of the carbon dioxide pressure. To the n-hexane layer in the washing device, there was added 6 ml of distilled water, the resulting mixture was stirred at the rate of 800 rpm at room temperature under the carbon dioxide atmosphere for 15 minutes and then allowed to stand. The upper n-hexane layer was removed from the system. To the aqueous layer, there were added sulfolane, triethylamine and water in amounts sufficient to replace the respective losses caused by addition to the n-hexane layer, and the resulting solution was returned under pressure to the 2,7-octadien-1-ol synthesis reactor. Following the above-mentioned procedure and using the same catalyst solution, 15 runs in total of the 2,7-octadien-1-ol synthesis followed by extraction with n-hexane were conducted. In any of the repeated runs, no supplemental portions of the palladium compound and organic phosphorus compound were added. Each n-hexane layer taken out from the system was assayed for products and sulfolane by gas chromatography, for triethylamine by titration, for water by Karl Fischer method, and for palladium and phosphorus compounds (each calculated as atom) by atomic absorption spectroscopy and colorimetry. The octadienol yield and the concentrations of the palladium and phosphorus compounds as found in the n-hexane layer are shown in Table 1 for the 4th, 7th, 10th and 15th runs.

TABLE 1

Results of repeated runs

| Run No. | Octadienols[a] Yield (g) | [b] | Catalyst component concentration in n-hexane layer (ppm) Palladium | Phosphorus |
|---|---|---|---|---|
| 4 | 66.0 | 93/7 | 0.28 | 1.7 |
| 7 | 65.3 | 93/7 | 0.23 | 1.7 |
| 10 | 65.2 | 94/6 | 0.24 | 1.6 |
| 15 | 66.8 | 93/7 | 0.30 | 2.0 |

[a] In addition to octadienols, there were formed 1,3,7-octatriene and vinylcyclohexene (2.0-2.4 g in total), and dioctadienyl ether (0.5-0.6 g).
[b] Molar ratio of 2,7-octadien-1-ol to 1,7-octadien-3-ol.

As can be seen in Table 1, the catalytic activity and the extent of elution of the catalyst components into the n-hexane layer did not change but remained constant, without being influenced by the repeated use of the catalyst solution. In run No. 15, about 85 percent of the octadienols formed were extracted into the n-hexane layer.

(ii) Separation of n-hexane from the n-hexane layer

A 2-liter glass distillation device was charged carefully in a nitrogen atmosphere with 1 liter of the n-hexane layer collected throughout the repeated runs mentioned above under (i), which layer contained, per liter thereof, about 18 g of butadiene, 550 g of n-hexane, 101.2 g of 2,7-octadien-1-ol, 7.6 g of 1,7-octadien-3-ol, 3.6 g of 1,3,7-octatriene plus vinylcyclohexene, 1.0 g of dioctadienyl ether, 5.3 g of sulfolane, 1.6 g of triethylamine bicarbonate (corresponding to 1.0 g of triethylamine), 0.1 g of water, 0.24 ppm of palladium, and 1.8 ppm (as phosphorus atom) of the phosphorus compound. Distillation was performed at an atmospheric pressure while keeping the bottom temperature at 90° C. or below, whereby 508 g of n-hexane containing triethylamine and water each in a very small amount was recovered. The distillation residue was transferred to a 500-ml glass distillation device containing 25 g of distilled water, and distillation was conducted under atmospheric pressure, whereby 44.7 g of a fraction boiling at up to 90° C. was collected. The fraction contained 41 g of n-hexane, 0.8 g of triethylamine, 0.2 g of 1,3,7-octatriene plus vinylcyclohexene, and 2.7 g of water. The bottom liquid was transferred to a separatory funnel and allowed to stand at about 40° C., whereby it separated into two layers. Assays revealed that the organic layer (upper layer; 139 ml) contained 101.1 g of 2,7-octadien-1-ol, 7.6 of 1,7-octadien-3-ol, 3.4 g of 1,3,7-octatriene plus vinylcyclohexene, 1.0 g of dioctadienyl ether, 4.3 g of water, 3.4 g of sulfolane, 0.1 g of triethylamine, 0.83 ppm of palladium, 3.4 ppm (as phosphorus atom) of the phosphorus compound, and only a trace amount of n-hexane. During the above distillation operation, apparent deposition of metallic palladium was not observed. The above-mentioned procedure was followed repeatedly (six times in all), to give a total of about 830 ml of an organic layer predominantly composed of 2,7-octadien-1-ol. Throughout the distillation procedure, the utmost care was taken to prevent air from entering the device.

(iii) Separation of octadienols from the organic layer

Using a packed distillation column with 15 theoretical plates, 725 g of the organic layer obtained by the procedure mentioned above under (ii) mainly composed of 2,7-octadien-1-ol was distilled at a reduced pressure of 70 mmHg. The foregoing runs contained water, triethylamine, 1,3,7-octatriene, vinylcyclohexene, 1,7-octadien-3-ol and 2,7-octadien-1-ol. The main fraction boiling at 108°-126° C. subsequently amounted to 633 g and was a mixture of 2,7-octadien-1-ol and 1,7-octadien-3-ol in the molar ratio of 93/7. To the distillation residue (36.5 g), there was added 30 g of water, and the mixture was shaken and then allowed to stand, whereby it separated into two layers. Analysis of the upper organic layer revealed that said layer was predominantly composed of 2,7-octadiene-1-ol and dioctadienyl ether whereas most of the sulfolane and catalyst components had migrated to the lower aqueous layer.

(iv) Hydrogenation of 2,7-octadien-1-ol

A one-liter stainless steel autoclave equipped with thermometer, magnetic stirrer, liquid metering and feeding pump, hydrogen gas inlet, off gas flow meter, and liquid outlet was charged with 1.5 g of nickel-on-diatomaceous earth catalyst (Nissan-Girdler's G-69; Ni content 52 percent by weight) and 100 g of n-octanol. After sufficiently replacing the atmosphere with hydrogen gas, the system was heated to 160° C. with stirring. Then, the octadienol mixture obtained by the procedure mentioned above under (iii) was continuously fed to the system at the rate of 70 g per hour at the temperature of 160° C., hydrogen pressure of 10 kg/cm² (gauge), rate of stirring of 500 rpm and off gas flow rate of 30 liters per hour, with stirring for 7 hours. After effecting the hydrogenation reaction in this manner, octadienol mixture feeding, hydrogen gas introduction and stirring were discontinued, and the reaction mixture was immediately removed from the system via the liquid outlet. After removing the catalyst by filtration, the mixture was analyzed by gas chromatography, whereupon it was revealed that the average conversion of octadienols to octanols was 98.5 percent and that the hydrogenation product contained small amounts of intermediary hydrogenation products, namely octenols. The filtrate obtained upon separation of the catalyst by filtration was charged into the above-mentioned autoclave. The autoclave was connected via the liquid feeding pump to a column hydrogenation reactor (50 mm in inside diameter and 250 mm in column length) packed with a nickel-on-diatomaceous earth (Nissan-Girdler's G-49B; Ni content 55 percent by weight) in the form of cylinders (3/16"×⅛"), containing 123 g of n-octanol, and fitted with a jacket. The autoclave and packed column were heated to 130° C., and hydrogen was introduced to the pressure of 5 kg/cm² (gauge). The autoclave contents were saturated with hydrogen gas by stirring at the rate of 400 rpm. After the internal temperature and hydrogen pressure respectively became constant, the mixture was continuously fed from the autoclave to the bottom of the packed column hydrogenation reactor at the rate of 450 ml/hr (corresponding to the liquid space velocity of 3 hr$^{-1}$). The hydrogenated mixture was continuously taken out from the top of the packed column into a one-liter reservoir autoclave by the overflow method. The finishing hydrogenation was carried out under said conditions continuously for 90 minutes. Gas chromatography and ultraviolet absorption spectrometry of the mixture taken out did not reveal the presence of octenols and octanals within the limits of analytical error.

(v) Separation of n-octanol

Using a packed column type distillation device with 30 theoretical plates, 400 ml of the mixture of n-octanol and 3-octanol as obtained by the procedure mentioned above under (iv) was distilled at a reduced pressure of 100 mmHg, whereby 17.4 g of 3-octanol was obtained as a fraction boiling at 114°–116° C. and 285 g of n-octanol as a fraction boiling at 135°–136° C. High boiling substances were practically absent in the distillation residue. Gas chromatography and ultraviolet absorption spectrometry confirmed that the n-octanol fraction was of a very high purity.

The octadienol synthesis was conducted under the same conditions and using the same procedure mentioned above under (i) except that various kinds of phosphines, solvents and amines were used in place of sodium m-(diphenylphosphino)benzenesulfonate dihydrate, sulfolane and triethylamine. Three runs in total of octadienol synthesis were conducted. The n-octadienol yields as found in the n-hexane layer are shown in Table 2 for the 3rd runs.

TABLE 2

Effect of solvent, phosphine and amine on the catalytic activity

| Experimental No. | Solvent | Phosphine | Amine | Octadienol yield (g) | n/i | Selectivity[1] |
|---|---|---|---|---|---|---|
| 1 | Sulfolane | 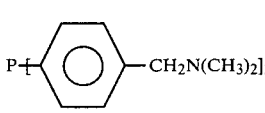 $P[\!-\!\langle C_6H_4\rangle\!-\!CH_2N(CH_3)_2]_3$ | $(C_2H_5)_3N$ | 62 | 92/8 | 90 |
| 2 | Sulfolane | 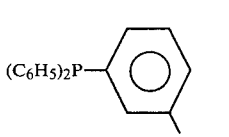 $(C_6H_5)_2P\!-\!\langle C_6H_4\rangle\!-\!COOLi$ | N—methylmorpholine | 55 | 95/5 | 89 |
| 3 | Sulfolane | 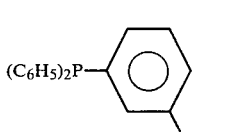 $(C_6H_5)_2P\!-\!\langle C_6H_4\rangle\!-\!SO_3Na$ | none | 15 | 92/8 | 91 |
| 4 | t-Butanol | 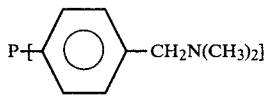 $P[\!-\!\langle C_6H_4\rangle\!-\!CH_2N(CH_3)_2]_3$ | $(C_2H_5)_3N$ | 7 | 71/29 | 67 |
| 5 | Acetone | 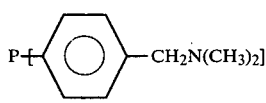 $P[\!-\!\langle C_6H_4\rangle\!-\!CH_2N(CH_3)_2]_3$ | $(C_2H_5)_3N$ | 8 | 53/47 | 49 |
| 6 | Dioxane | 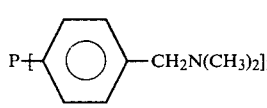 $P[\!-\!\langle C_6H_4\rangle\!-\!CH_2N(CH_3)_2]_3$ | $(C_2H_5)_3N$ | 5 | 48/52 | 46 |

TABLE 2-continued
Effect of solvent, phosphine and amine on the catalytic activity

| Experimental No. | Solvent | Phosphine | Amine | Octadienol yield (g) | | Selectivity[1] |
|---|---|---|---|---|---|---|
| 7 | N—methylpyrrolidone | 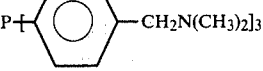 | $(C_2H_5)_3N$ | 16 | 70/30 | 61 |
| 8 | Acetonitrile | 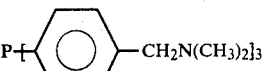 | $(C_2H_5)_3N$ | 12 | 81/19 | 69 |
| 9 | Dimethylsulfoxide |  | $(C_2H_5)_3N$ | 6 | 72/28 | 65 |
| 10 | N—methylmorpholine | 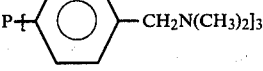 | $(C_2H_5)_3N$ | 4 | 62/38 | 66 |
| 11 | N,N'—dimethylformamide | 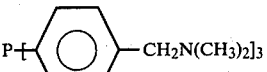 | $(C_2H_5)_3N$ | 6 | 77/23 | 71 |
| 12 | Sulfolane |  | Pyridine | 4 | 90/10 | 84 |
| 13 | Sulfolane | 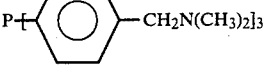 | α,α'-dipyridyl | 0 | — | — |
| 14 | Sulfolane |  | N,N,N',N'—tetra-methylethanediamine | 2 | 58/42 | 52 |
| 15 | water |  | $(C_2H_5)_3N$ | 1 | 89/11 | 46 |
| 16 | Sulfolane | $(C_6H_5)_3P$ | $(C_2H_5)_3N$ | 0 | — | — |

[1] 2,7-octadien-1-ol(mole)/whole reaction products (mole) × 100

Table 2 shows that the combination of sulfolane, phosphine and tertiary amine (pKa of 7 or more) afforded satisfactory results with respect to reaction rate and reaction selectivity.

EXAMPLE 2

Fifteen runs in all of 2,7-octadien-1-ol synthesis followed by extraction and isolation of 2,7-octadien-1-ol were repeatedly conducted following the same procedure under the same conditions as described under (i) in Example 1 except that 0.915 g (2.66 millimoles per liter of the liquid charge) of the hydrophilic bidentate phosphine

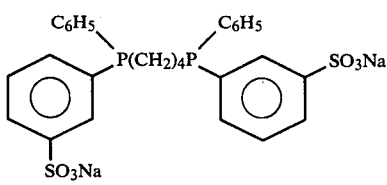

was additionally used as a component of the catalyst system and that cyclohexane was used as the extractant in place of n-hexane. For the 4th, 10th and 15th runs, the octadienol yields as found in the respective cyclohexane layers were 64.3 g, 61.8 g and 63.5 g, respectively, and the average concentrations of palladium and phosphorus (each calculated as atom) in the cyclohexane layer were 0.33 ppm and 2.8 ppm, respectively.

Following the procedure described in Example 1 under (ii), six one-liter portions (6 liters in total) of the cyclohexane layer collected by the above repetition of runs were subjected to distillation so as to remove cyclohexane and to give about 825 ml of an organic layer predominantly composed of 2,7-octadien-1-ol. In each distillation operation, the amount of distilled water used was 60 g. The organic layer was then distilled under reduced pressure (70 mmHg), followed by the procedure described in Example 1 under (iii), to give 605 g of a mixture of 1,7-octadien-3-ol and 2,7-octadien-1-ol (molar ratio 7/93) as a fraction boiling at 108°–126° C. This octadienol mixture was subjected to hydrogenation by the procedure described in Example 1 under (iv), and 400 ml of the reaction mixture obtained was subjected to fractional distillation by the procedure described in Example 1 under (v). There was thus obtained 275 g of n-octanol. Gas chromatography and ultraviolet absorption spectrometry confirmed that the n-octanol was at least 99.9 percent pure.

EXAMPLE 3

Further repetition (10 runs) of the procedures described in Example 1 under (i) and (ii) gave about 500 g of organic layer predominantly composed of 2,7-octadien-1-ol. The organic layer was distilled under reduced pressure (70 mmHg) using a packed column having 30 theoretical plates. Finally, there was obtained about 300 g of 2,7-octadien-1-ol as a fraction boiling at 125°–127° C. The 2,7-octadien-1-ol fraction was hydrogenated using the magnetically stirred autoclave described in Example 1 under (iv). Thus, the autoclave was charged with 2.0 g of 3% palladium on carbon catalyst and 50 g of n-octanol, the atmosphere was sufficiently replaced with hydrogen gas, and the system was heated to 80° C. (internal temperature) with stirring. The hydrogenation was then effected continuously for 4 hours with stirring under the conditions: temperature 80° C., hydrogen pressure 10 kg/cm$^2$ (gauge), rate of stirring 500 rpm, off gas flow rate 30 liters/hr, and 2,7-octadien-1-ol feed rate 70 g/hr. Thereafter, the feed of 2,7-octadien-1-ol was discontinued, and the stirring was continued under the same conditions for additional 60 minutes. The hydrogen gas introduction and stirring were then stopped, and the reaction mixture was taken out from the system via the liquid outlet. After separation of the catalyst by filtration, the mixture was analyzed by gas chromatography, whereby it was revealed that the mixture contained about 3% of n-octanal along with n-octanol. 2,7-octadien-1-ol and octenols were not detected. Using the same distillation column as used in (v) of Example 1, 350 ml of the hydrogenation reaction mixture was subjected to fractional distillation under reduced pressure (500 mmHg). There was obtained 255 g of n-octanol as a fraction boiling at 181°–182° C. The purity of the n-octanol as determined by gas chromatography and ultraviolet absorption spectrometry was at least 99.9 percent.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for producing n-octanol which comprises the steps of:
   (i) reacting butadiene with water in a solution containing 25–55 wt % water, 5–30 wt % of a carbonate and/or bicarbonate salt of a monodentate tertiary amine having a basicity constant (pKa) of not less than 7, and 30–65 wt % of sulfolane based on the reaction mixture, in the presence of a palladium compound and a hydrophilic monodentate phosphine in an amount of at least 6 moles per gram atom of palladium, to form 2,7-octadien-1-ol;
   (ii) extracting 2,7-octadien-1-ol from at least part of the reaction mixture obtained in step (i) with a saturated aliphatic hydrocarbon, a monoolefinic hydrocarbon or an alicyclic hydrocarbon, and recycling the extraction residue to the 2,7-octadien-1-ol synthesis step (i);
   (iii) subjecting the extract layer containing 2,7-octadien-1-ol as obtained in step (ii) to distillation at a liquid phase temperature of not higher than about 100° C. to distill off a large proportion of the extracting solvent therefrom, followed by distillation in the presence of water, whereby the extracting solvent remaining is distilled off in the form of an azeotropic mixture with water, to obtain a distillation residue;
   (iv) recovering 2,7-octadien-1-ol from the distillation residue obtained in step (iii) by distillation;
   (v) hydrogenating the 2,7-octadien-1-ol obtained in step (iv) in the presence of a hydrogenation catalyst to obtain n-octanol; and
   (vi) recovering n-octanol from the hydrogenation reaction mixture by distillation.

2. The process of claim 1, wherein, in step (i), the palladium compound is used in an amount corresponding to 0.1–50 milligram atoms of palladium per liter of the reaction mixture.

3. The process of claim 1, wherein, in step (i), the hydrophilic monodentate phosphine is used in an amount of 10–100 moles per gram atom of palladium.

4. The process of claim 1, wherein, in step (i), the tertiary amine carbonate and/or bicarbonate is triethylamine carbonate and/or bicarbonate.

5. The process of claim 1, wherein the hydrophilic monodentate phosphine used in step (i) is a compound of the general formula (I)

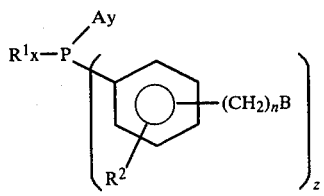

wherein $R^1$ is an aliphatic, alicyclic, or substituted or nonsubstituted aromatic hydrocarbon group containing up to 8 carbon atoms; $R^2$ is a hydrogen atom, a methyl, nitro, cyano or methoxy group or a halogen atom; n is an integer of 0 or 1, x is an integer of 0, 1 or 2, y and z are each an integer of 0, 1, 2 or 3 with the proviso that y and z are not concurrently equal to 0 and that $x+y+z=3$; A is $-CH_2CH(CH_3)COOM$, $-C(CH_3)_2COOM$, $-CH_2CH(CH_3)N(R^3)(R^4)$, $-C(CH_3)_2N(R^3)(R^4)$, a carbonate or bicarbonate of $-CH_2CH(CH_3)N(R^3(R^4)$, or a carbonate or bicarbonate of $-C(CH_3)_2N(R^3)(R^4)$; B is $-SO_3M$, COOM, $-N(R^3)(R^4)$ or a carbonate or bicarbonate of $-N(R^3)(R^4)$; $R^3$ and $R^4$ each being methyl, ethyl or n-propyl and M being an alkali metal.

6. The process of claim 1, wherein, in step (i), a hydrophilic bidentate phosphine is additionally used in an amount of 0.3–3 moles per gram atom of palladium.

7. The process of claim 6, wherein said hydrophilic bidentate phosphine is a compound of the general formula (II)

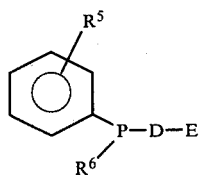

wherein $R^5$ is a hydrogen or halogen atom, a methyl, cyano, methoxy or nitro group, $-SO_3M$, $-COOM$, $-N(R^7)(R^8)$, $-CH_2N(R^7)(R^8)$, a carbonate or bicarbonate of $-N(R^7)(R^8)$ or a carbonate or bicarbonate of $-CH_2N(R^7)(R^8)$ wherein $R^7$ and $R^8$ each being methyl, ethyl or n-propyl and M being an alkali metal, $R^6$ is a hydrocarbon group containing up to 8 carbon atoms, D is $-(CH_2)_n-$ where n is an integer of 1 through 4,

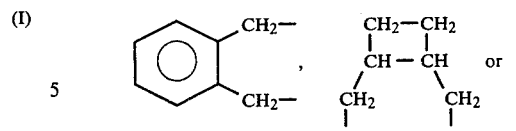

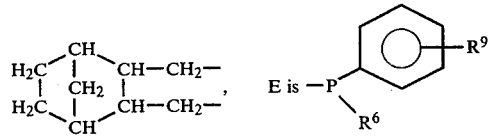

wherein $R^9$ is $-SO_3M$, $-COOM$, $-N(R^7)(R^8)$, $-CH_2N(R^7)(R^8)$, a carbonate or bicarbonate of $-N(R^7)(R^8)$ a carbonate or bicarbonate of $-CH_2N(R^7)(R^8)$, $-N(R^7)(R^8)$, a carbonate or bicarbonate of $N(R^7)(R^8)$, or $-COOM$.

8. The process of claim 1, wherein the reaction mixture fed to step (ii) has an 2,7-octadien-1-ol concentration of 0.3–2 moles per liter of the reaction mixture.

9. The process of claim 1, wherein the extraction in step (ii) is performed in a carbon dioxide atmosphere at a temperature of not higher than about 60° C.

10. The process of claim 1, wherein the extractant used in step (ii) is a saturated aliphatic hydrocarbon selected from the group consisting of n-pentane and n-hexane or an alicyclic hydrocarbon selected from the group consisting of cyclohexane and methylcyclohexane.

11. The process of claim 1, wherein, in step (ii), the extractant is used in an amount of 0.3–3 parts by volume per part by volume of the reaction mixture.

12. The process of claim 1, wherein the hydrogenation in step (v) comprises preliminary hydrogenation and finishing hydrogenation.

13. The process of claim 1, wherein the hydrogenation catalyst is a palladium-on-carrier catalyst, a Raney nickel catalyst, a modified Raney nickel catalyst, a nickel-on-carrier catalyst or a ruthenium catalyst.

14. The process of claim 12, wherein the hydrogenation percentage in the preliminary hydrogenation is at least 90 percent.

15. The process of claim 12, wherein the finishing hydrogenation is performed in the gaseous or liquid phase in a column packed with a nickel- or ruthenium-on-carrier catalyst.

* * * * *

UNITED STATES PATENT AND TRADEMARK OFFICE
CERTIFICATE OF CORRECTION

PATENT NO. : 4,417,079
DATED : November 22, 1983
INVENTOR(S) : NORIAKI YOSHIMURA ET AL It is certified that error appears in the above-identified patent and that said Letters Patent is hereby corrected as shown below:

Column 1, delete lines 12-17, and insert therefor

-- $2\ CH_2=CH-CH=CH_2 + H_2O$ $\longrightarrow CH_2=CHCH_2CH_2CH_2CH=CHCH_2OH$ 2,7-octadien-1-ol $CH_2=CHCH_2CH_2CH_2CH=CHCH_2OH + 2\ H_2$ $\longrightarrow CH_3CH_2CH_2CH_2CH_2CH_2CH_2CH_2OH$ n-octanol --.

Column 1, lines 48-49, delete "2,7-octadiene-1-ol", and insert therefor -- 2,7-octadien-1-ol --.

UNITED STATES PATENT AND TRADEMARK OFFICE
CERTIFICATE OF CORRECTION

PATENT NO. : 4,417,079

DATED : November 22, 1983

INVENTOR(S) : NORIAKI YOSHIMURA ET AL

It is certified that error appears in the above-identified patent and that said Letters Patent is hereby corrected as shown below:

Column 2, line 64, delete "II", first and second occurrences, and insert therefor -- $\pi$ --.

Column 3, line 2, delete "II", and insert therefor -- $\pi$ --.

Column 3, line 44, delete "or", second occurrence, and insert therefor -- of --.

Column 4, line 11, delete "or", and insert therefor -- of --.

Column 6, line 27, delete "or", third occurrence, and insert therefor -- of --.

Column 6, line 30, delete "carbonatoms", and insert therefor -- carbon atoms --.

UNITED STATES PATENT AND TRADEMARK OFFICE
CERTIFICATE OF CORRECTION

PATENT NO. : 4,417,079
DATED : November 22, 1983
INVENTOR(S) : NORIAKI YOSHIMURA ET AL Page 3 of 4

It is certified that error appears in the above-identified patent and that said Letters Patent is hereby corrected as shown below:

Column 6, line 50, delete " , " and insert therefor -- ; --.

Column 6, line 51, delete "or", first occurrence, and insert therefor -- of --, and delete " , " and insert therefor -- ; --.

Column 8, lines 36 and 39, delete "2,7-octadiene-1-ol", and insert therefor -- 2,7-octadien-1-ol --.

Column 14, line 50, delete "2,7-octadiene-1-ol", and insert therefor -- 2,7-octadien-1-ol --.

Column 17, Table 2, Experimental No. 11, delete "N,N'", and insert therefor -- N,N --.

Column 20, line 20, before "water", insert -- of --.

UNITED STATES PATENT AND TRADEMARK OFFICE
CERTIFICATE OF CORRECTION

PATENT NO. : 4,417,079
DATED : November 22, 1983
INVENTOR(S) : NORIAKI YOSHIMURA ET AL    Page 4 of 4

It is certified that error appears in the above-identified patent and that said Letters Patent is hereby corrected as shown below:

Column 21, line 21, delete "$(R^3(R^4)$", and insert therefor -- $(R^3)(R^4)$ --.

Column 21, line 22, before "COOM", insert -- — --.

Column 22, line 18, delete "," both occurrences, and insert therefor -- ; --.

Column 22, line 19, delete "," and insert therefor -- ; --.

Signed and Sealed this

Twenty-seventh Day of May 1986

[SEAL]

Attest:

DONALD J. QUIGG

Attesting Officer    Commissioner of Patents and Trademarks